United States Patent [19]

Rosok et al.

[11] Patent Number: 5,716,829
[45] Date of Patent: Feb. 10, 1998

[54] **DIAGNOSTIC TEST FOR *PSEUDOMONAS AERUGINOSA* INFECTIONS**

[75] Inventors: Mae Joanne Rosok, Seattle; Mark E. Lostrom, Redmond; Richard P. Darveau, Kirkland, all of Wash.

[73] Assignee: Genetic Systems Corporation, Redmond, Wash.

[21] Appl. No.: 452,845

[22] Filed: May 30, 1995

Related U.S. Application Data

[63] Continuation of Ser. No. 226,434, Apr. 12, 1994, abandoned, which is a continuation of Ser. No. 717,875, Jun. 18, 1991, abandoned, which is a continuation of Ser. No. 552,376, Jul. 16, 1990, abandoned, which is a continuation of Ser. No. 349,874, May 9, 1989, abandoned, which is a continuation of Ser. No. 3,671, Jan. 15, 1987, abandoned.

[51] Int. Cl.$^6$ ................................................. G01N 33/569
[52] U.S. Cl. .................... 435/7.32; 435/7.1; 435/961; 435/962; 435/975; 436/172; 436/175; 436/825; 530/388.4; 530/391.1; 530/399.3
[58] Field of Search ......................... 435/7.32, 961, 435/962, 975, 7.1; 530/388.4, 391.1, 399.3; 436/172, 175, 825

[56] References Cited

U.S. PATENT DOCUMENTS

| 4,452,903 | 6/1984 | Lee et al. | 436/540 |
| 4,596,769 | 6/1986 | Shockman et al. | 435/7.32 |

FOREIGN PATENT DOCUMENTS

| 063986 | 11/1982 | European Pat. Off. | 435/7.32 |
| 076695 | 4/1983 | European Pat. Off. | |

OTHER PUBLICATIONS

Gosting et al, "Identification of a Species–Specific Antigen in *Legionella pneumophila* by a Monoclonal Antibody", J. Clin. Microbiol., 20(6): 1031–1035(Dec. 1984).

Mutharia et al, "Characterization of Two Surface–Localized Antigenic Sites on Porin Protein F of *Pseudomonas aeruginosa*", Can J. Microbiol., 31:381–386 (1985).

Nixdorff et al, "Interaction of Lipopolysaccharide with Detergents and its Possible Role in the Detergent Resistance of the Outer Membrane of Gram–Negative Bacteria", Biochim. Biophys. Acta, 510:87–98 (1978).

Mutharia et al, Abstract No.:33069r "Surface Localization of *Pseudomonas aeruginasa* Outer Membrane Porin Protein F by Using Monoclonal Antibodies", Chem Abstract, 100: 333 (1984).

Gray et al. "The Effect of Ethylenediaminetetra–acetic Acid on the Cell Wall of Some Gram–Negative Bacteria", *J. Gen. Microbiol.* 39:385–399 (1965).

Matsushita et al. "Isolation and Characterization of Outer and Inner Membranes from *Pseudomonas aeruginosa* and Effect of EDTA on the Membranes", *J. Biochem.* 83:171–181 (1978).

Kohler et al., "Rapid Diagnosis of *Pseudomonas aeruginosa* Urinary Tract Infections by Radioimmunoassay", *J. Clin. Microbiol.* 9:253–258 (1979).

Yoshimura et al., "Purification and Properties of *Pseudomonas aeruginosa* Porin", *J. Biol. Chem.* 258:2308–2314 (1983).

Gosting et al. "Identification of Species–Specific Antigen in *Legionella pneumophila* by a Monoclonal Antibody", *J. Clin. Microbiol.* 20:1031–1035 (1984).

Pennington et al. "Polyclonal and Monoclonal Antibody Therapy for Experimental *Pseudomonas aeruginosa* Pneumonia", *Infect. & Immun.* 54:239–244 (1986).

Gordon et al. "Rapid Identification of *Pseudomonas aeruginosa* Using Panreactive Monoclonal Antibody", *Canadian J. Med. Tech.* 49:22–27 (1987).

Counts et al. "Evaluation of Immunofluorescent–Antibody Test for Rapid Identification of *Pseudomonas aeruginosa* in Blood Cultures", *J. Clin. Microbiol.* 26:1161–1165 (1988).

Cook et al., "Detection of *Pseudomonas aeruginosa* Antigen in Serum using a Panreactive Monoclonal Antibody", *Clin. & Invest. Med.* Abst. 31B (1982).

Ajello et al., Invest. Urology (1967) 5:203–212.

Sands et al., J. Clin. Path. (1975) 28:997–999.

Kohler et al., J. Clin. Microbiol. (1979) 9:253–258.

Hancock et al., Biochim. Biophys. Acta (1979) 554:323–331.

Hancock and Carey, J. Bacteriol. (1979) 140:902–910.

Hedstrom et al., J. Bacteriol. (1981) 148:995–997.

Gilleland et al., Infect. Immun. (1984) 44:49–54.

Yoshimura et al., J. Biol. Chem. (1983) 258:2308–2314.

Mutharia et al., Infect. Immun. (1983) 42:1027–1033.

Mutharia et al., Can. J. Microbiol. (1985) 31:381–386.

Hancock et al., Adv. Exp. Med. Biol. (1985) 185:215–222.

Hancock et al., Eur. J. Clin. Microbiol. (1985) 4:224–227.

Hancock et al, Adv. Exp. Med. Biol., 185:215–222 (1985).

Mutharia et al, Can. J. Microbiol., 31:381–386 (1985).

*Primary Examiner*—Jeffrey Stucker
*Attorney, Agent, or Firm*—Townsend and Townsend and Crew LLP

[57] ABSTRACT

Methods and reagents are provided for a novel immunodiagnostic test for the presence of *P. aeruginosa* in a biological sample. Monoclonal antibodies are employed which bind to an outer membrane protein antigen, which may be exposed by a solubilizing reagent. The antibody binds substantially all strains of *P. aeruginosa*. No cross-reactivity with other species of Pseudomonas or with other clinically significant gram-negative or gram-positive species is observed. Conjugating the monoclonal antibody of the invention with a fluorescent label provides for a rapid and sensitive direct immunofluorescent test for *P. aeruginosa*.

17 Claims, No Drawings

DIAGNOSTIC TEST FOR *PSEUDOMONAS AERUGINOSA* INFECTIONS

This application is a continuation of U.S. application Ser. No. 08/226,434, filed Apr. 12, 1994, now abandoned, which is a continuation of U.S. application Ser. No. 07/717,875, filed Jun. 18, 1991, now abandoned, which is a continuation of U.S. application Ser. No. 07/552,376, filed Jul. 16, 1990, now abandoned, which is a continuation of U.S. application Ser. No. 07/349,874, filed May 9, 1989, now abandoned, which is a continuation of U.S. application Ser. No. 07/003,671, filed Jan. 15, 1987, now abandoned.

TECHNICAL FIELD

This invention relates generally to the use of novel immunological compositions and methods in the diagnosis of infections caused by *Pseudomonas aeruginosa*. More particularly, a sensitive and specific immunofluorescence test employing monoclonal antibodies to an outer membrane protein of *P. aeruginosa* is described.

BRIEF DESCRIPTION OF THE BACKGROUND ART

Gram-negative bacterial infections are the cause of significant morbidity and mortality in human patients. Infections due to one such gram-negative organism, *P. aeruginosa*, are recognized by the medical community as particularly difficult to treat. A patient's prognosis for recovery from an infection caused by *P. aeruginosa* is enhanced when the diagnosis is made and appropriate treatment initiated as early in the course of the infection as possible, before the number of bacteria in the host becomes overwhelming and much more difficult to bring under control.

The diagnosis of *P. aeruginosa* infections is currently based upon clinical findings, microbiological cultures and biochemical tests. While the rapid and accurate diagnosis of *P. aeruginosa* infections is highly desireable, it is not currently possible using existing reagents and techniques. Gram stains of direct smears from patients are of little or no value. The only truly reliable method to date is the isolation of the bacterium in pure culture and its subsequent identification by biochemical or serological methods. Conventional laboratory culture techniques involve incubating clinical samples for 24–48 hours to allow the organisms to multiply to macroscopically detectable levels. Subculture techniques and metabolic assays are then required to distinguish *P. aeruginosa* from related pseudomonads and other enteric bacteria and may require an additional 24–48 hrs.

In an effort to speed up and simplify the diagnostic process for the often life-threatening infections caused by *P. aeruginosa*, several immunological approaches have been attempted. The immunofluorescent detection of *P. aeruginosa* using polyclonal antisera produced in rabbits is described in Ajello et al., Invest. Urology, 5:203 (1967); Sands et al., *J. Clin. Path.*, 28:997 (1975); and Kohler et al., *J. Clin. Microbiol.*, 9:253 (1979). Due to a variety of problems inherent in such preparations, these reagents have not found acceptance in clinical laboratories.

Monoclonal antibody technology was pioneered by the work of Kohler and Milstein, *Nature* 256:495 (1975). Monoclonal antibodies can now be produced in virtually unlimited quantities consistently and with a high degree of purity. These qualities facilitate the reproducibility and standardization of performance of diagnostic tests which are required in hospitals and other clinical settings.

Monoclonal antibodies have been produced against several components of the complex outer membrane of *P. aeruginosa*. Several monoclonal antibodies have been described that bind to *P. aeruginosa*'s lipopolysaccharide, including the O-side chains, core and lipid A portions of the molecule. Monoclonals that bind to the O-side chains are generally serotype or immunotype specific, however, and are inadequate by themselves to detect all serotypes or immunotypes of *P. aeruginosa*. Monoclonal antibodies that bind to the core and lipid A portions are nonspecific, in that they are capable of also binding to other species of Pseudomonas or other gram-negative bacteria.

The outer membrane of *P. aeruginosa* also contains several polypeptides in addition to its lipopolysaccharide component. One of these proteins, protein F, is present in large numbers in the membrane and forms water-filled channels through the membrane's hydrophobic core. Mutharia and Hancock have described the preparation and characterization of several murine monoclonal antibodies to porin protein F in the outer membrane of *P. aeruginosa* (Infect. Immun. 42:1027 (1983); *Can. J. Microbiol.*, 31:381 (1985); and Adv. Exp. Med. Biol., 185:215 (1985)) all of which are incorporated herein by reference.

Immunofluorescence staining methods can be divided into two categories, direct and indirect. In the direct staining method, a fluorophore is conjugated to an antibody (hereinafter called the "primary antibody") which is capable of binding directly to the cellular antigen of interest. In the indirect staining mode, the primary antibody is not fluorescently labeled; its binding is visualized instead by the binding of a fluorescently labeled second-step antibody, which second-step antibody is capable of binding to the primary antibody. Typically, the second-step antibody is an anti-immunoglobulin antibody. In some instances the second-step antibody is unlabeled and a third-step antibody which is capable of binding the second-step antibody is fluorescently labeled.

Indirect immunofluorescence is sometimes advantageous in that it can be more sensitive than direct immunofluorescence because for each molecule of the primary antibody which is bound, several molecules of the labeled second-step antibody can bind. However, it is well known that indirect immunofluorescence is more prone to nonspecific staining than direct immunofluorescence, that is, staining which is not due to the specific antigen-antibody interaction of interest (Johnson et al., in *Handbook of Experimental Immunology*, D. M. Weir, ed., Oxford: Blackwell Publications (1979) and Mishell et al., ed., *Selected Methods in Cellular Immunology*, San Francisco: W. H. Freeman (1980) ). In addition, the multiple steps involved in performing the indirect tests makes them slow, labor intensive, and more susceptible to technician error.

Despite the availability of monoclonal antibodies to several structural components of *P. aeruginosa*, including protein F, there remains a significant and urgent need in hospitals and clinical laboratories for a rapid, sensitive and accurate diagnostic test for *P. aeruginosa*. The present invention fulfills this need.

SUMMARY OF THE INVENTION

Briefly stated, novel reagents and methods are provided for the detection and diagnosis of *P. aeruginosa* in biological specimens. The method comprises reacting a specimen suspected of containing the organism with a monoclonal antibody or fragment thereof capable of binding to an outer membrane protein antigen shared by substantially all serotypes or immunotypes of *P. aeruginosa*, separating the specimen from unbound antibody, and detecting the presence of immune complexes formed between the monoclonal antibody and the *P. aeruginosa* antigen and therefrom determining the presence of *P. aeruginosa*. Novel hybrid cell lines are also provided which produce the monoclonal antibodies capable of specifically binding to protein F of *P. aeruginosa*. When the monoclonal antibodies are labeled and combined with a solubilizing reagent, a specific and rapid direct test for *P. aeruginosa* is achieved.

DESCRIPTION OF THE SPECIFIC EMBODIMENTS

In accordance with the present invention, novel compositions of monoclonal antibodies are provided where such antibodies are capable of selectively binding to *P. aeruginosa* and therefore may be utilized as a diagnostic test. The monoclonal antibodies of this invention can be prepared by immortalizing the expression of nucleic acid sequences which code for antibodies specific for protein F of *P. aeruginosa*. This may be accomplished by introducing such sequences, typically cDNA encoding for the antibody, into a host capable of cultivation and culture. The immortalized cell line may be a mammalian cell line that has been transformed through oncogenesis, by transfection, mutation, or the like. Such cells include myeloma lines, lymphoma lines, or other cell lines capable of supporting the expression and secretion of the antibody in vitro. The antibody may be a naturally occurring immunoglobulin of a mammal other than human, produced by transformation of a lymphocyte, by means of a virus or by fusion of the lymphocyte with a neoplastic cell, e.g., a myeloma, to produce a hybrid cell line. Typically, the lymphoid cell will be obtained from an animal immunized against protein F or a fragment thereof containing an epitopic site.

Immunization protocols are well known and can vary considerably yet remain effective. See Golding, *Monoclonal Antibodies: Principles and Practice*, (1983) which is incorporated herein by reference. Immunogenic amounts of antigenic preparations are injected, generally at concentrations in the range of 1 ug to 20 mg/kg of host. The antigenic preparation used to immunize the animal will preferably comprise those protein F molecules which are retained by the peptidoglycan molecules of the cell wall after treatment with detergent, as discussed further below. Administration of the antigenic preparations may be one or a plurality of times, usually at one to four week intervals. Immunized animals are monitored for production of antibody to the desired antigens, the spleens are then removed and splenic B lymphocytes isolated and transformed or fused with a myeloma cell line. The transformation or fusion can be carried out in conventional ways, the fusion technique being described in an extensive number of patents, e.g. U.S. Pat. Nos. 4,172,124; 4,350,683; 4,363,799; 4,381,292; and 4,423,147. See also, Kennett et al. *Monoclonal Antibodies* (1980) and references therein, and Golding, Supra.

The hybrid cell lines may be cloned and screened in accordance with conventional techniques, and antibodies in the cell supernatants detected that are capable of binding to protein F of *P. aeruginosa*. The appropriate hybrid cell lines may then be grown in large scale culture in vitro or injected into the peritoneal cavity of an appropriate host for production of ascites fluid. By virtue of having the antibody of the present invention, which is known to be specific for protein F, the supernatants may be screened in competition with the subject monoclonal antibodies in a competitive assay. Thus, hybrid cell lines can be readily produced from a variety of sources based on the availability of the present antibodies specific for the particular antigen. Alternatively, these hybrid cell lines may be fused with other neoplastic B cells, or such other B cells may serve as recipients for genomic DNA coding for the antibody. Or, using hybrid DNA techniques, the monoclonal antibody may be an immunoglobulin produced by inserting genomic DNA or cDNA coding for one or both heavy and light chains into an expression vector for expression of the chains. See, for example, European Patent Publications Nos. 171,496 and 173,494.

While rodent, particularly murine, neoplastic B cells are preferred, other mammalian species may be employed, such as lagomorpha, bovine, ovine, equine, porcine, avian or the like. Immunization of these animals can be readily performed and their lymphocytes, particularly, splenocytes, may be obtained for fusions.

The monoclonal antibodies secreted by the transformed or hybrid cell lines may be of any of the classes or subclasses of immunoglobulins, such as IgM, IgD, IgA, or subclasses of IgG known for each species of animal. As IgG is the most common isotype utilized in diagnostic assays, it is preferred for this purpose. The monoclonal antibodies may be used intact, or as fragments, such as Fv, Fab, F(ab')$_2$, but usually intact.

Monoclonal antibodies of the present invention are particularly useful for diagnostic purposes. Typically, the diagnostic assay will entail the detection of the formation of a complex through the binding of the monoclonal antibody to a particular epitope on the protein F antigen of *P. aeruginosa*. Hybridomas producing monoclonal antibodies capable of binding to or forming immune complexes with different antigenic epitopes or domains are included within this invention. Monoclonal antibodies capable of blocking the binding of antibodies produced by the hybrid cell line of the present invention, such as ATCC No. HB9277 described below are preferred.

For use in diagnostic assays the antibodies of the present invention may be directly labeled. A wide variety of labels may be employed, such as radionuclides, fluorescers, enzymes, enzyme substrates, enzyme cofactors, enzyme inhibitors, ligands (particularly haptens), etc. When unlabeled, the antibodies may find use in agglutination assays. In addition, unlabeled antibodies can be used in combination with other labeled antibodies (second antibodies) that are reactive with the monoclonal antibody, such as antibodies specific for the immunoglobulin. Numerous types of immunoassays are available and are well known to those skilled in the art.

In general, it is necessary to at least partially purify the primary antibody from the ascites fluid or culture supernatants before labeling. Methods of purification are well known (Mishell et al., supra), and can include ammonium sulfate fractionation, ion exchange chromatography, gel filtration chromatography, affinity chromatography, or some combination thereof.

Because of the ready availability of fluorescence microscopes in the clinical laboratory, the preferred labeling substance in the instant invention is a fluorophore, typically fluorescein, rhodamine, phycoerythrin, or phycocyanin. Methods of labeling antibodies with fluorophores are known in the art (Weir, supra). Typically, antibody is incubated with fluorescein isothiocyanate (FITC) at an approximate ratio of 45 ug FITC per mg of antibody protein for about one hour at 37° C. Labeled antibody is separated from free label by gel filtration, for example, on Sephadex G-25. Labeling with phycoerythrin or phycocyanin is typically accomplished as described by Oi et al., *J. Cell. Biol.*, 93:981 (1982) and in U.S. Pat. No. 4,520,110.

The biological specimen to be assayed for the presence of *P. aeruginosa* can be prepared in a variety of ways, depending on the source of the specimen. The specimen may be a sample of human blood, sputum, urine, wound exudate, or human tissues or a laboratory culture thereof. Desireably, prior to or at the time of combining the primary antibody with the specimen, the specimen will be treated with a surfactant or solubilizing reagent which will expose antigenic determinants of protein F which are not otherwise readily accessible to the antibody compositions. These solubilizing agents include detergents such as Triton X-100 (Triton is a registered trademark of Rohm and Haas Co., for octylphenoxypolyethoxyethanol) and sodium deoxycholate. A combination of solubilizing agents, such as Triton X-100, with a chelating agent, such as ethylenediaminetetraacetic acid (EDTA), is preferred. The concentration of Triton X-100 is usually about 0.05% to 2.5% (v/v), preferably about 0.5% (v/v), and the concentration of EDTA may range from 1 mM up to about 100 mM, but is preferably about 9 mM. The solubilizing step is performed in an appropriately buffered medium, usually PBS at an alkaline or neutral pH, usually from pH 7.0 to pH 9.3, preferably pH 9.3. This technique appears to release from the outer membrane the protein F molecules which are not associated with the peptidoglycan of the bacterial cell wall as well as the cell's lipopolysaccharide molecules, as the cell is not reactive with anti-LPS antibodies after the desired treatment. This may expose epitopes or domains of protein F not otherwise accessible on untreated cells. The antibodies of the present invention react with those molecules of protein F which remain associated with the peptidoglycan after Triton$^{(R)}$ X-100 and EDTA treatment. If the solubilization step occurs simultaneously with the addition of the primary antibody, care should be taken to ensure that the antibody remains stable and reactive with its binding partner under the solubilizing conditions employed. One must also be careful not to solubilize all of the porin protein F molecules attached to the peptidoglycan structure.

The biological sample suspected of containing *P. aeruginosa* is combined with the primary antibody under conditions conducive to immune complex formation. If the test is a one-step immunofluorescence assay the primary antibody will be labeled. Typically, the specimen is first fixed or adhered to a glass slide by heat and/or ethanol treatment, although other fixatives or adherents are known by those skilled in the art. The specimen is then contacted with the solubilizing agent for a sufficient period, usually from 1 to 30 minutes and more usually about 10 minutes, and the solubilizer is then washed from the slide. Alternatively, as described above, the solubilizing agent and the primary antibody may be combined and added as one step. The primary antibody should be incubated with the specimen for approximately 30 minutes at room temperature, although the conditions may be varied somewhat. The slide is rinsed to remove unbound antibody. If the primary antibody has been labeled with FITC, the reacted sample may be viewed under a fluorescence microscope equipped with standard fluorescein filters (excitation=490 nm; emission=520 nm) and a 40X oil immersion lens. The quantitation of fluorescence is based on visual observation of the brightness or relative contrast of the specifically stained antigen. Appropriate positive and negative controls make interpretation more accurate. A counterstain, such as Evans blue, may be employed to more easily visualize the fluorescent organisms.

The subject invention may be used to specifically recognize the presence of *P. aeruginosa* in clinical specimens or laboratory cultures. The monoclonal antibody does not cross react with other clinically important gram-negative or gram-positive organisms or other species of Pseudomonas with which the invention was tested, as listed in Table I. It is believed that substantially all isolates of the various serotypes or immunotypes *P. aeruginosa* may be recognized by the antibodies, whereas it is believed that no species of Pseudomonas other than *P. aeruginosa* is detected. For a review of typing schema for *P. aeruginosa*, see Zierdt, C. H. in *Glucose Nonfermenting Gram-Negative Bacteria in Clinical Microbiology*, Gilardi, G. L., ed., CRC Press, pp. 213–238 (1978) and the more recently proposed International Antigenic Typing Scheme (IATS) system in Liu, P. V., Int. J. Syst. Bacteriol., 33:256-264 (1983). Thus, desireably at least 90–95%., usually 95–99%, and preferably greater than 99% of clinical isolates of *P. aeruginosa* are detected with the present invention. Moreover, none of the non-Pseudomonas species cross-react with the antibodies disclosed herein with the exception of an organism termed "CDC-Group I," a heterogeneous group of organisms rarely isolated from humans.

Kits can also be supplied for use with the subject antibodies in the detection of *P. aeruginosa*, wherein said kits comprise compartments containing a monoclonal antibody capable of reacting with essentially all serotypes and immunotypes of *P. aeruginosa*, and labels and necessary reagents for providing a detectable signal. Thus, the monoclonal antibody composition of the present invention may be provided, usually in a lyophilized form, either alone or in conjunction with additional antibodies specific for other antigens of *P. aeruginosa*. The antibodies, which may be conjugated to a label, are included in the kits with buffers, such as Tris, phosphate, carbonate, etc., stabilizers, biocides, inert proteins, e.g. bovine serum albumin, or the like. Generally, these materials will be present in less than about 5% weight based on the amount of active antibody, and usually present in total amount of at least about 0.001% weight based again on the antibody concentration. Frequently, it will be desirable to include an inert extender or excipient to dilute the active ingredients, where the excipient maybe present in from about 1% to 99% weight of the total composition. Where a second antibody capable of binding to the monoclonal antibody is employed, this will usually be present in a separate vial. The second antibody may be conjugated to a label and formulated in a manner analogous to the antibody formulations described above.

Other features and advantages of the present invention will become apparent from the following experimental descriptions, which describe the invention by way of example. The examples are offered by way of illustration and not byway of limitation.

EXAMPLE I

Example I demonstrates the methodology used to prepare a murine monoclonal antibody that binds specifically to *P. aeruginosa* protein F.

Purification of Protein F.

Six liters of L broth (1% [w/v] Difco broth, 1%[w/v] Difco yeast extract, 0.5% [w/v] sodium chloride) were inoculated with *P. aeruginosa* Fisher immunotype 5 (A.T.C.C 27316) from an overnight trypticase soy agar slant culture. The broth culture was grown overnight at 37° C. with aeration and the bacteria were harvested and washed as described by Yoshimura et al. (*J. Biol. Chem.*, 258:2308, (1983). The bacteria were disrupted by sonication (Braun-Sonic 1510) and the outer membranes isolated by centrifugation at 100,000×g. Protein F was isolated from the outer membranes by repeated extractions in lithium dodecyl sulfate, released from the peptidoglycan by heating, and then separated from other outer membrane proteins by gel filtration on a Sephacryl$^{(R)}$ 200 column (Pharmacia, Piscataway, N.J.) as described by F. Yoshimura, et al. supra. elution of proteins was monitored by the absorbance at 280 nm, and aliquots of the major peak fractions were examined by sodium dodecyl sulfate polyacrylamide gel electrophoresis (SDS-PAGE) according to the method of Lugtenberg et al., (FEBS Lett., 58:254, 1978) as modified by Hancock et al. (*J. Bacteriol.*, 140:902, 1979). Aliquots were solubilized in SDS sample buffer, 0.125M Tris-HCl, pH 6.8, 2% (w/v) SDS, 10% (v/v) glycerol, and 0.005% (w/v) bromophenol blue and then heated ten minutes at 85°–95° C. Electrophoresis was performed for 16 hours at a constant voltage of 55–60V. Molecular weight standards (phosphorylase B, 92,500 molecular weight [MW]; bovine serum albumin, 66,200 MW; ovalbumin, 45,000 MW; soybean trypsin inhibitor, 21,500 MW; lysozyme, 14,400 MW)(Bio-Rad Laboratories, Richmond, Calif.) were included in the same polyacrylamide gel. The molecular weight of the protein isolated from this major peak was 35,000 daltons, which is the molecular weight of protein F (Hancock et al. and Yoshimura, et al. supra). The protein was greater than 95% pure as judged by Coomassie blue staining of the gel.

Preparation of a Murine Monoclonal Antibody that Binds Protein F.

Three month old BALB/c mice were extensively immunized over a six month period with a variety of antigen preparations. Mice were initially injected three times with *P. aeruginosa* Fisher immunotype 7 (A.T.C.C. 27318) bacteria which had been heat-killed by autoclaving for 30 minutes, followed by three injections with *P. aeruginosa* Fisher immunotype 7 lipopolysaccharide (LPS) (20–50 ug per mouse) purified by the method of Westphal et al., *Methods in Carbohydrate Chemistry*, 5:83 (1985) Academic Press, N.Y. The mice were then immunized twice with viable *P. aeruginosa* Fisher immunotype 6 (A.T.C.C. 27317) bacteria, first with $1 \times 10^7$ organisms and then with $3.4 \times 10^7$ organisms. The mice then received four weekly injections of outer membranes purified from *P. aeruginosa* Fisher immunotype 6 organisms according to the method of Hancock et al. (J. Bacteriol., 136:381, 1978) in combination with purified *P. aeruginosa* protein F. The dosage of outer membranes administered was 80–100 ug protein per injection, and the initial dosage of protein F was 5 ug and was increased over the course of the four injections such that the final dosage was 20 ug.

Three days after the last injection, the spleen from one mouse was removed aseptically and a single cell suspension was prepared by gentle rotation of the organ between the frosted ends of two sterile glass slides. Spleen menonuclear cells were combined in a 3:1 ratio with log phase mouse myeloma cells (NSI-1, obtained from Dr. C. Milstein, Molecular Research Council, Cambridge, England) and fused to create hybridomas according to the procedure described by Tam et al. (Infect. Immun., 36:1042, 1982). The final hybrid cell suspension was diluted to a concentration of $1.5 \times 10^6$ cells per ml in RPMI-hybrid-HAT (RPMI 1640 [Gibco, Grand Island, N.Y.] containing 15% heat-inactivated fetal calf serum, 1 mM sodium pyruvate, 100 ug/ml of streptomycin and 100 IU/ml penicillin, $1.0 \times 10^{-4}$M hypoxanthine, $4.0 \times 10^{-7}$M aminopterin, and $1.6 \times 10^{-5}$M thymidine) which included $2.0 \times 10^6$ per ml freshly prepared BALB/c thymocytes as feeder cells. The mixture was plated (200 ul per well) into 96-well Costar plates. Cultures were fed by removal and replacement of 50% of the volume of each well with fresh RPMI-hybrid-HAT every two to three days. Culture supernatants were assayed for the presence of anti-*P. aeruginosa* protein F antibodies by enzyme-linked immunosorbant assay (ELISA) when the cell growth reached approximately 40% confluency in the wells on the seventh day after the fusion.

Anti-protein F antibodies present in culture supernatants were detected by ELISA on antigen coated plates. Purified protein F, 1.5 ug per ml in 0.05M bicarbonate buffer, pH 9.6, was added to 96-well tissue culture plates (Linbro) (50 ul per well) and incubated 1 hr. at 37° C. in a humidified chamber. Unbound antigen was removed by first flicking the buffer out of the wells and then washing the wells three times with phosphate-buffered saline (PBS), pH 7.2 (100 ul per well). To prevent non-specific reactions, potentially reactive sites were blocked by adding 5% (w/v) bovine serum albumin (BSA) in PBS (5% BSA-PBS)(75 ul per well) to the plates and incubating for 45 min. at 37° C. After flicking out the unadsorbed BSA, culture supernatants (50 ul) from each well of the fusion plates were replica-plated into the corresponding wells of the antigen plates and incubated 30 min. at 37° C. The unbound antibody was flicked out of the wells and the plates washed three times with 100 ul 1% (w/v) BSA-PBS. Next, 50 ul per well of horseradish peroxidase-conjugated protein A (Zymed Laboratories, South San Francisco, Calif.) appropriately diluted in 1% BSA-PBS was added to the plates and incubated 30 min. at room temperature. The plates were washed as described above and then substrate (100 ul per well) was added. The substrate was prepared by solubilizing one tablet of chromagen, o-phenylenediamine-2 HCl (Organon Diagnostic, Orange, N.J.) in 22 ml 0.1M citrate buffer, pH 5, and then mixing the solution with an equal volume of 0.03% (v/v) $H_2O_2$ just prior to use. Reactions were terminated after 30 min. at room temperature in the dark with 3N $H_2SO_4$ (50 ul per well). Hybridoma cells secreting monoclonal antibodies that bound to protein F were located by measuring the colorimetric reactions in each well at an absorbance of 490 nm with an automated ELISA reader.

The cells in one well, designated PaPor5 IG1, produced antibody that bound to protein F. PaPor5 IG1 cells from the master well were low density subcultured and then cloned by limiting dilution techniques as described by Tam, et al., supra. The monoclonal antibody and the clonal cell line from this well are both identified by the PaPor5 IG1 designation in the following text. The cells in another well, designated IG12, also produced antibody that reacted with protein F.

Ascites fluid containing high titred monoclonal antibody was obtained from BALB/c Nu/Nu mice or ( BALB/c [female]×C57B1/6 [male]$_{F1}$ mice according to procedures described by Tam, et al., supra. Two to three month old male mice were injected intraperitoneally with 0.5 ml Pristane (2,6,10,14-Tetramethylpentadecane, Aldrich Chemical Co., Milwaukee, Wis.) 10–21 days prior to intraperitoneal injection with log phase PaPor5 IG1 cells. Each mouse was injected with $5.0 \times 10^6$ cells in 0.5 ml RPMI. After approximately two weeks the ascites fluid that accumulated was removed from the mice every two to three days. The concentration of antibody in the ascites fluid was determined by agarose gel electrophoresis (Paragon, Beckman Instruments, Inc., Brea, Calif.), and all ascites that contained 5 mg/ml or greater antibody was pooled, aliquoted, and frozen at −70° C.

Confirmation of Specificity of PaPor5 IG1 by Immunoblot

The reaction of PaPor5 IG1 with *P. aeruginosa* protein F was confirmed by Immunoblot (Towbin, et al., Proc. Natl. Acad. Sci. USA, 76:4350, 1979). Purified *P. aeruginosa* protein F was applied to a 14% SDS polyacrylamide gel as described above. Prestained molecular weight markers (lysozyme, 14,300 MW; beta-lactoglobulin, 18,400 MW; alphachymotrypsinogen, 25,700 MW; ovalbumin, 43,000 MW; bovine serum albumin, 68,000 MW; phosphorylase B, 97,400 MW; and myosin, 200,000 MW) (BRL, Gaithersburg, Md.) were included in the same polyacrylamide gel. After electrophoresis, protein F was transferred to a nitrocellulose membrane (NCM) (0.45 um, Schleicher & Schuell, Inc., Keene, N.H.) by electro-phoresis in 25 mM sodium phosphate, pH 7.2 for 1–2 hrs. at 27V (Bittner, et al., Anal. Biochem., 1:459 (1980)). After transfer the NCM was incubated in 0.5% (v/v) Tween-20 in PBS (PBS-Tween) (Batteiger et al., J. Immunol. Meth., 55:297 (1982)) for 1 hr. at room temperature. For this step and all subsequent steps, the tray containing the NCM was placed on a rocking platform to ensure distribution of solution over the entire NCM. After 1 hr. the PBS-Tween solution was poured off and the NCM was cut into strips. One strip was incubated with culture supernatant containing PaPor5 IG1 monoclonal antibody, a second was incubated with culture supernatant containing an irrelevant anti-P. aeruginosa exopolysaccharide murine monoclonal antibody, and a third with culture media. After an incubation of 1 hr. at room temperature, the NCM strips were washed five times, five min. each, with PBS-Tween to remove unbound antibody. Alkaline phosphatase-conjugated goat anti-mouse IgG (Zymed Laboratories, Inc., South San Francisco, Calif.) was diluted according to manufacturer's specifications and incubated with the NCM strips for one hour at room temperature. After the NCMs were washed five times as described above, substrate containing bromochloroindolyl phosphate and nitroblue tetrazolium (Sigma, St. Lous, Mo.) prepared as described by Leary, et al. (Proc. Natl. Acad. Sci. USA, 80:4045 (1983)) was added and incubated 10–20 min. at room temperature. The reaction was terminated by washing substrate away with distilled water. Results of the experiment showed that PaPor5 IG1 bound specifically to purified protein F. No staining of the protein F band was observed on the NCM strips incubated with either the anti-exopolysaccharide monoclonal antibody or the culture media. In a similar experiment using culture supernatant from the cells designated IG12, the antibody produced by this cell line was also found to be specifically reactive with protein F.

EXAMPLE II

Example II describes the direct conjugation of the murine monoclonal antibody, PaPor5 IG1, with fluorescein isothiocyanate (FITC) and its use in identifying P. aeruginosa.

PaPor5 IG1 antibody was purified by protein A - sepharose chromatography (Ey, P. L., et al., 1978, Immunochemistry, 15:429) and then dialyzed at 4° C. overnight into conjugation buffer, 0.29M carbonate/bicarbonate, pH 9.3, 1 M NaCl. Following dialysis, 80 ul of antibody (5 mg/ml) was combined with 2 ul of fluorescein-5- isothiocyanate (FITC)(Lot 5E, isomer I, F-143, Molecular Probes, Inc., Junction City, Oreg.) solubilized in dimethyl sulfoxide at a concentration of 24 mg/ml just prior to use. After an incubation of 30 min. at 37° C. the mixture was passed over a PD-10 Sepharose$^{(R)}$ column (Pharmacia, Piscataway, N.J.) pre-equilibrated in 0.01 M carbonate/bicarbonate, pH 9.3 buffer, containing 1.0 M NaCl, 0.1 mg/ml bovine serum albumin, and 0.01% sodium azide. The FITC-conjugated antibody was collected in the void volume.

The bacteria for the assay were prepared from overnight cultures on an appropriate solid medium. The organisms were resuspended in PBS and the optical density adjusted to a McFarland 2 standard. The suspended organisms were then spotted onto 30-well Carlson slides (Carlson, Peotone, Ill.)(2 ul per well) and air dried at room temp. The slides were stored at −70° C. with a dessicant until used in the assay.

On the day of the assay the prepared slides of bacteria were first fixed in 95% ethanol for 10 min. at room temp. After the ethanol evaporated from the slides by heating at 37° C. on a slide warmer, they were treated with 0.5% (v/v) Triton-X 100$^{(R)}$ and 9 mM EDTA in PBS (3 ul per well) for 10 min. at room temp. The slides were then washed with distilled water for 1 min. and dried at 37° C. FITC-conjugated PaPor5 IG1 (66 ug/ml) was added (5 ul per well) and incubated 30 min. at room temp. in a humidified chamber. The slides were washed and dried as above, covered with a coverslip mounted with PBS/glycerol (1:1 v/v), pH 9.8 containing 2.5% (w/v) triethylenediamine to stabilize the fluorescein, and viewed with a fluorescent microscope. The results are shown in Table I. Panel A shows the results for 30 different isolates of P. aeruginosa, including the seventeen IATS type strains and representatives of six of seven Fisher immunotypes. Panel B comprises 17 species of Pseudomonas other than P. aeruginosa. Panel C shows the results for 29 other organisms from a variety of gram-positive and gram-negative bacteria other than Pseudomonas. As can be seen in Table I PaPor5 IG1 demonstrated strong immunofluorescence with all strains of P. aeruginosa. Among other species of Pseudomonas tested, none demonstrated detectable levels of immunofluorescence with the subject antibodies. Among the non-Pseudomonas species tested, only an organism classified as belonging to CDCGroup I showed detectable levels of reactivity.

Since the intensity of fluorescence of organisms bound by the FITC-conjugated antibodies is an important consideration in the utility of a slide immunofluorescence test, the test was performed under conditions similar to that for clinical blood cultures. A P. aeruginosa strain was inoculated into either Bactec$^R$ Broth (Johnston Laboratories, Townson, Md.) or a biphasic broth (PML Microbiologicals, Tualatin, Oreg.) containing 5 ml of normal blood. After incubation at 37° C. for 8 hr, visible turbidity was observed and an aliquot of the culture was removed for the direct immunofluorescence test. As mall drop of the blood broth was placed in a well on a slide and was combined with a drop of deionized water to lyse the red blood cells. The mixture was spread evenly over the entire well and allowed to dry. The sample was then fixed with ethanol and the assay performed as described above. The fluorescence of the P. aeruginosa strain was 4+, whereas no immunofluorescence was observed when Escherichia coli, a common blood pathogen, was examined in the same manner.

Although the foregoing invention has been described in some detail by way of illustration and example for purposes of clarity and understanding, it will be obvious that certain changes and modifications maybe practiced within the scope of the appended claims.

TABLE I

Results of Direct Immunofluorescence Assay for *P. aeruginosa* Using FITC-Conjugated PaPor5 IG1 on Bacterial Isolates

| Organism | Results |
|---|---|
| Panel A | |
| 1. *Pseudomonas aeruginosa* IATS 1 | 4+ |
| 2. *Pseudomonas aeruginosa* IATS 2 | 4+ |
| 3. *Pseudomonas aeruginosa* IATS 3 | 4+ |
| 4. *Pseudomonas aeruginosa* IATS 4 | 4+ |
| 5. *Pseudomonas aeruginosa* IATS 5 | 4+ |
| 6. *Pseudomonas aeruginosa* IATS 6 | 4+ |
| 7. *Pseudomonas aeruginosa* IATS 7 | 4+ |
| 8. *Pseudomonas aeruginosa* IATS 8 | 4+ |
| 9. *Pseudomonas aeruginosa* IATS 9 | 4+ |
| 10. *Pseudomonas aeruginosa* IATS 10 | 4+ |
| 11. *Pseudomonas aeruginosa* IATS 11 | 4+ |
| 12. *Pseudomonas aeruginosa* IATS 12 | 4+ |
| 13. *Pseudomonas aeruginosa* IATS 13 | 4+ |
| 14. *Pseudomonas aeruginosa* IATS 14 | 4+ |
| 15. *Pseudomonas aeruginosa* IATS 15 | 4+ |
| 16. *Pseudomonas aeruginosa* IATS 16 | 4+ |
| 17. *Pseudomonas aeruginosa* IATS 17 | 4+ |
| 18. *Pseudomonas aeruginosa* Fisher 1 | 4+ |
| 19. *Pseudomonas aeruginosa* Fisher 1 | 4+ |
| 20. *Pseudomonas aeruginosa* Fisher 1 | 4+ |
| 21. *Pseudomonas aeruginosa* Fisher 1 | 4+ |
| 22. *Pseudomonas aeruginosa* Fisher 2 | 4+ |
| 23. *Pseudomonas aeruginosa* Fisher 2 | 4+ |
| 24. *Pseudomonas aeruginosa* Fisher 2 | 4+ |
| 25. *Pseudomonas aeruginosa* Fisher 2 | 4+ |
| 26. *Pseudomonas aeruginosa* Fisher 3 | 4+ |
| 27. *Pseudomonas aeruginosa* Fisher 3 | 4+ |
| 28. *Pseudomonas aeruginosa* Fisher 4 | 4+ |
| 29. *Pseudomonas aeruginosa* Fisher 5 | 4+ |
| 30. *Pseudomonas aeruginosa* Fisher 6 | 4+ |
| Panel B | |
| 31. *Pseudomonas maltophilia* | 0 |
| 32. *Pseudomonas testosteroni* | 0 |
| 33. *Pseudomonas mendocina* | 0 |
| 34. *Pseudomonas picketti* | 0 |
| 35. *Pseudomonas putrefaciens* | 0 |
| 36. *Pseudomonas stutzeri* | 0 |
| 37. *Pseudomonas pseudoalcaligenes* | 0 |
| 38. *Pseudomonas vesiculare* | 0 |
| 39. *Pseudomonas fluorescens* | 0 |
| 40. *Pseudomonas putida* | 0 |
| 41. *Pseudomonas alcaligenes* | 0 |
| 42. *Pseudomonas cepacia* | 0 |
| 43. *Pseudomonas acidovorans* | 0 |
| 44. *Pseudomonas diminuta* | 0 |
| 45. *Pseudomonas paucimobilis* | 0 |
| 46. *Pseudomonas pertucinogena* | 0 |
| 47. *Pseudomonas aureofaciens* | 0 |
| Panel C | |
| 48. *Acinetobacter calcoaceticus* var. *anitratum* | 0 |
| 49. *Actinomyces israelli* | 0 |
| 50. *Bacteroides fragilis* | 0 |
| 51. *Bacteroides oralis* | 0 |
| 52. *Bifidobacterium dentium* | 0 |
| 53. *Campylobacter sputorum* ssp. *bubulus* | 0 |
| 54. *Corynebacterium ulcerans* | 0 |
| 55. *E. coli* | 0 |
| 56. *Klebsiella pneumoniae* | 0 |
| 57. *Enterobacter cloacae* | 0 |
| 58. *Proteus mirabilis* | 0 |
| 59. *Eubacterium limosum* | 0 |
| 60. *Fusobacterium nucleatum* | 0 |
| 61. *Haemophilus influenzae* (untypeable) | 0 |
| 62. CDC — Group I | 4+ |
| 63. *Haemophilus influenzae* type B | 0 |
| 64. *Lactobacillus catenaforme* | 0 |
| 65. *Leptotrichia buccalis* | 0 |
| 66. *Micrococcus luteus* | 0 |
| 67. *Moraxella lacunata* | 0 |
| 68. *Neisseria meningitidis* | 0 |
| 69. *Neisseria sicca* | 0 |
| 70. *Legionella pneumophila* serogroup 1 | 0 |
| 71. *Peptococcus asaccharolyticus* | 0 |
| 72. *Peptostreptococcus anaerobius* | 0 |
| 73. *Rothia dentocariosa* | 0 |
| 74. *Cardiobacterium hominis* | 0 |
| 75. *Staphylococcus aureus* ("Woods") | 0 |
| 76. *Staphylococcus epidermidis* | 0 |
| 77. *Treponema denticola* | 0 |

Results were scored on a 0 to 4+ scale according to intensity of immunofluorescence staining, with 0 being negative, 1+ the least intense and 4+ the brightest.

What is claimed is:

1. A method for the detection and diagnosis of the bacterium *Pseudomonna aeruginosa* in biological specimens, said method comprising:
   reacting a specimen suspected of containing said bacterium with a detergent, EDTA, and a monoclonal antibody or fragment thereof capable of specifically binding to outer membrane peptidoglycan-bound bound protein F antigen of said bacterium and not substantially reactive with other species of *Pseudomonas*, wherein said reacting does not solubilize all peptidoglycan-bound protein F antigen;
   separating said specimen from unbound monoclonal antibody; and
   detecting the presence or absence of immune complexes formed between said monoclonal antibody and said antigen.

2. The method of claim 1 wherein said detection of immune complexes is by a label.

3. The method of claim 2 wherein the label is selected from the group consisting of fluorophores, enzymes, luminescent compounds, radioisotopes and particles.

4. The method of claim 3 wherein the fluorophore is one selected from the group consisting of fluorescein, rhodamine, phycoerythrin, and phycocyanin.

5. The method of claim 2 wherein the label is a fluorophore.

6. The method of claim 5 wherein the fluorophore is fluorescein isothiocyanate.

7. The method of claim 2, wherein the monoclonal antibody thereof is directly labeled.

8. The method of claim 1 further comprising immobilizing said specimen on a solid surface before contacting said specimen with the detergent and EDTA.

9. The method of claim 1 wherein the detergent is octylphenoxypolyethoxyethanol.

10. The method of claim 1, wherein the specimen is contacted with the detergent and EDTA prior to reacting with the monoclonal antibody.

11. A method for detecting the bacterium *Pseudomonas aeruginosa* in a biological specimen, said method comprising:
   reacting the specimen with a detergent, EDTA, and a monoclonal antibody or fragment thereof capable of specifically binding to an epitope of outer membrane peptidoglycan-bound protein F common to *P. aeruginosa* and not substantially reactive with other species of Pseudomonas, wherein said reacting does not solubilize all peptidoglycan-bound protein F antigen; and detecting the presence of immune complexes formed between said monoclonal antibody and said epitope and therefrom determining the presence of said bacterium.

12. The method of claim 11 further comprising, after the reacting step, separating said specimen from the unbound monoclonal antibody.

13. The method of claim 11 wherein the monoclonal antibody is labeled.

14. A kit for use in detecting the presence of *Pseudomonas aeruginosa*, said kit comprising compartments containing a monoclonal antibody composition wherein said monoclonal antibody reacts with peptidoglycan-bound protein F common to *P. aeruginosa*, a detergent and EDTA and labels providing for a detectable signal covalently bonded to said antibodies or bonded to second antibodies or reagents reactive with said monoclonal antibody.

15. A method for the detection of the bacterium *Pseudomonas aeruginosa* in a biological sample, said method comprising:

contacting said sample with a detergent and EDTA, reacting said sample with a monoclonal antibody or binding fragment thereof which specifically binds to peptidoglycan-bound protein F antigen common to *P. aeruginosa* and not substantially reactive with other species of Pseudomonas, wherein said reacting does not solubilize all peptidoglycan-bound protein F antigen; and detecting the presence of immune complexes formed between said antibody and said antigen.

16. The method of claim 15 wherein the detergent is octylphenoxypolyethoxyethanol.

17. The method of claim 15 wherein said monoclonal antibody is produced by hybrid cell line PaPor5 IG1 (ATCC #HB9277).

* * * * *